(12) United States Patent
Agdeppa et al.

(10) Patent No.: US 7,906,106 B2
(45) Date of Patent: *Mar. 15, 2011

(54) IN VIVO CELL TRAFFICKING

(75) Inventors: Eric Dustin Agdeppa, Fairview, NJ (US); Srabani Bhaumik, Niskayuna, NY (US); June Klimash, Nikayuna, NY (US); Jeannette Christine DePuy, Watervliet, NY (US); Anton Beletskii, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 728 days.

This patent is subject to a terminal disclaimer.

(21) Appl. No.: 11/769,085

(22) Filed: Jun. 27, 2007

(65) Prior Publication Data

US 2009/0004115 A1    Jan. 1, 2009

(51) Int. Cl.
*A61B 10/00* (2006.01)
*A61B 5/00* (2006.01)

(52) U.S. Cl. ........ 424/9.6; 424/1.11; 424/1.65; 424/9.1; 424/9.2

(58) Field of Classification Search .................. 424/1.11, 424/1.37, 1.49, 1.65, 1.69, 1.81, 9.1, 9.2, 424/9.3, 9.4, 9.5, 9.6, 9.7, 9.8
See application file for complete search history.

(56) References Cited

U.S. PATENT DOCUMENTS

| 6,217,847 | B1 | 4/2001 | Contag et al. |
| 6,534,041 | B1 | 3/2003 | Licha et al. |
| 7,776,553 | B2 * | 8/2010 | Love et al. ..................... 435/7.1 |
| 2003/0186348 | A1 | 10/2003 | Thomas et al. |
| 2004/0057903 | A1 | 3/2004 | Hancu et al. |

FOREIGN PATENT DOCUMENTS

| WO | WO9935288 | 7/1999 |
| WO | WO9951270 | 10/1999 |
| WO | WO9958161 | 11/1999 |
| WO | WO2006065146 | 6/2006 |

OTHER PUBLICATIONS

Weissleder, Ralph et al, "In Vivo Imaging of Tumors with Protease-Activated Near-Infrared Fluorescent Probes", Nature Biotechnology, vol. 17, Apr. 1999, pp. 375-378.
Mahmood, Umar et al, "Near-Infrared Optical Imaging of Protease Activity for Tumor Detection", Radiology 1999, 213: 866-870.
Galande, Amit K. et al, "Enzyme-Targeted Fluorescent Imaging Probes on a Multiple Antigenic Peptide Core", J. Med. Chem., 2006, 49, 4715-4720.
Josephson, Lee et al., "Near-Infrared Fluorescent Nanoparticles as Combined MR/Optical Imaging Probes", Bioconjugate Chem., 2002, 13, 554-560.

* cited by examiner

*Primary Examiner* — D L Jones
(74) *Attorney, Agent, or Firm* — Jenifer E. Haeckl (57) ABSTRACT

Provided herein are methods of monitoring inflammatory cell migration in a mammal. The methods include the steps of: providing a donor mammalian subject; introducing an inflammatory agent into the donor mammal to create a granuloma; isolating granuloma-derived nucleated cells from the granuloma of the donor mammalian subject; labeling the granuloma-derived nucleated cells with an optical agent; providing a recipient mammalian subject with inflamed tissue; introducing the granuloma-derived nucleated cells into a recipient mammalian subject at a site remote from site where the inflammatory agent was introduced; and imaging the recipient mammalian subject using an optical system. The methods may also include analysing the distribution of the labeled granuloma-derived cells in the recipient mammal.

35 Claims, 6 Drawing Sheets

IN VIVO CELL TRAFFICKING

BACKGROUND

Inflammatory responses within blood vasculature and tissue result in the recruitment of immune response cells to the site of disease or injury. Immune response cells (e.g., macrophage cells, dendritic cells, polynuclear monocytes (PNMs), eosinophils, neutrophils, and T cells) are know to participate in immune responses that cause inflammatory diseases, including diseases of the central nervous system, vascular disease, and autoimmune disease.

The compositions and methods of the present invention harness inflammatory response cells to deliver optical imaging agents from a remote site to the inflammatory foci to facilitate tracking of the progression of activated immune response cells through the body and into the inflamed tissue.

BRIEF DESCRIPTION

Provided herein are methods of monitoring inflammatory cell migration in a mammal. In some embodiments, the methods include the steps of: providing a donor mammalian subject; introducing an inflammatory agent (e.g., carrageenan) into the donor mammal to create a granuloma; isolating granuloma-derived nucleated cells from the granuloma of the donor mammalian subject; staining the granuloma-derived nucleated cells with an optical agent; providing a recipient mammalian subject with inflamed tissue; introducing the granuloma-derived nucleated cells into a recipient mammalian subject at a site remote from site where the inflammatory agent was introduced; and imaging the recipient mammalian subject using an optical system. The present methods may also include a step of determining the distribution of the labeled granuloma-derived cells in specific tissue and/or organs.

The donor and recipient mammalian subject may be any mammal, including without limitation a mouse, a rat, or a guinea pig. Each of the donor mammalian subject, the recipient mammalian subject, or both the donor mammalian subject and the recipient mammalian subject may be immunocomprosimsed. In some embodiments, both the donor mammalian subject and the recipient mammalian subject are histocompatible with each other.

The inflammatory agent may be introduced into the donor mammalian subject locally (e.g., subcutaneously) rather than systemically. The isolating may occur after about 1 day, about 3 days, or about 6 days following the introducing step.

The isolated granuloma-derived nucleated cells may be enriched using one or more enrichment techniques, for example, gravity sedimentation, density gradient enrichment, or affinity enrichment. Thus, the granuloma-derived may be enriched using an antibody or antibodies specific for cell surface antigen expressed by a cell population of interest (e.g., anti-CD45, anti-CD11b, or a combination of anti-CD45 and anti-CD11b). The optical imaging agent may comprise any fluorescent dye, for example a cyanine dye (e.g., Cye 5.5 and Cye 7.5) or a rotaxane dye.

The granuloma-derived nucleated cells (e.g., about 0.25 million to about 5 million) are introduced into the recipient mammalian subject through any parental method (e.g., intravenously).

The optical imaging step may be performed at wavelength frequency of about 440 nm to about 800 nm. In some embodiments, the wavelength frequency is about 766 nm to about 800 nm. In some specific embodiments, the wavelength is 785 nm.

The disclosed methods may further comprise the step of determining the presence of the ex vivo cells in the recipient mammalian subject using total photon counts. In some embodiments, the total photon counts are measured at from about 5 minutes to about 10 days after the injection of the granuloma-derived nucleated cells into the recipient mammalian subject.

The methods of monitoring inflammatory cell migration in a mammal provided herein may optionally include performing one or more biodistribution studies to determine the presence of the granuloma-derived nucleated cells in the recipient mammalian subject. In some embodiments, the biodistribution analysis may comprise extracting the liver, spleen, lung, and/or tumor tissue from the recipient mammalian subject and optically imaging the extracted tissue. Furthermore, the intensity of fluorescent emission of the optical imaging agent present in the extracted tissue may be measured and correlated to the amount of the amount of granuloma-derived nucleated cells present in the extracted tissue.

BRIEF DESCRIPTION OF THE DRAWINGS

These and other features, aspects, and advantages of the present invention will become better understood when the following detailed description is read with reference to the accompanying figures wherein:

FIG. 4 shows the granuloma localization of granuloma-derived nucleated cells in a recipient animal at day 5 in a prone position (FIG. 4A; CD1 mouse), a prone position (FIG. 4B; nude mouse).

DETAILED DESCRIPTION

The following detailed description is exemplary and not intended to limit the invention of the application and uses of the invention. Furthermore, there is no intention to be limited by any theory presented in the preceding background of the invention of the following detailed description of the drawings.

Definitions

To more clearly and concisely describe and point out the subject matter of the claimed invention, the following definitions are provided for specific terms, which are used in the following description and the appended claims.

As used herein, the term "granuloma-derived cells" refers to the activated inflammatory response cell whose cell surface receptors have interacted with the specific antigen introduced into the donor mammalian subject and comprise the contents of the granuloma produced at the site in which the inflammation-inducing agent (e.g., carrageenan) is introduced.

As used herein, the phrase "condition associated with immune cell accumulation" refers to physiological conditions wherein disease or injury causes immune cells (e.g., leukocytes, macrophages, or monocytes) to migrate to the affected tissue and accumulate at the location of disease or injury. Conditions associated with immune cell accumulation may include, for example, ischemia-reperfusion, atherosclerosis, renal failure, endometriosis, and autoimmune diseases such as multiple sclerosis and rheumatoid arthritis.

As used herein, the phrase "ex vivo" with regard to the introduction of optical imaging agents to a body refers to processes for obtaining and manipulating cells obtained from a subject outside the subject's body. In some embodiments, ex vivo processing includes removing inflammatory response cells from a subject's body, introducing optical imaging agents into the inflammatory response cells, and introducing the inflammatory response cells containing the optical imaging agents into a second subject's body. In some embodiments, the inflammatory response cells that are removed from the subject may be enriched (e.g., by FACS sorting, magnetic bead separation, or fractionation) for a particular class inflammatory response cell or particular classes of inflammatory response cells.

As used herein, with regard to the introduction optical imaging agents to a body, the phrase "in vivo" refers to methods for directly administering the disclosed optical imaging agents to the subject's body under conditions where endogenous inflammatory response cells take up the optical imaging agents within the subject's body. The agents of the present invention or their pharmaceutically acceptable salts can be administered to the subject in a variety of forms adapted to the chosen route of administration.

As used herein, the term "inflamed tissue" includes tissues that have elevated inflammatory response cells infiltrates. Inflamed tissue may be characterized by one or more of the following: (1) dilation of capillaries to increase blood flow to the affected area; (2) changes in the microvasculature structure, leading to the escape of inflammatory response cells from circulation; and/or (3) inflammatory response cells migrating from the capillaries and accumulating at the site of inflammation.

As used herein, the term "inflammatory response cell" refers to those cells that are stimulated by an immune response, whether the immune response results from injury, foreign antigen(s), and/or self antigen(s). Thus, inflammatory response cells include monocytes, macrophage, dendritic cells (DCs), polynuclear monocytes (PNMs), eosinophils, neutrophils, and T cells.

As used herein, the term "optical imaging agent" refers to fluorescent dyes with high extinction coefficients (>75,000), with quantum efficiencies greater than 0.1 and emissions above 600 nm. Exemplary, non-limiting examples of optical imaging agents include Cy5, Cy5.5, Cy7, Cy7.5, CypHer, IRDye 800, IRDye 680, Atto 647, Atto 655, Atto 740, Dy652, Dy734, Alexa 647, Alexa 680, and Alexa 750.

As used herein the term "pharmaceutically acceptable carrier" refers to those compounds which are, within the scope of sound medical judgment, suitable for use in contact with the tissues of a subject without undue toxicity, irritation, allergic response, and the like, commensurate with a reasonable benefit/risk ratio, and effective for their intended use, as well as salts and biocompatible derivatives of those compounds.

Embodiments

Unless otherwise indicated, all numbers expressing quantities of ingredients, properties such as molecular weight, reaction conditions, so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least each numerical parameter should at least be construed in light of the number of reported significant digits and by applying ordinary rounding techniques.

Mammalian subjects. The mammalian subjects may be any mammalian species. In some embodiments, the mammalian subject may be a mouse, a rat, a guinea pig, or any other small animal that is used in pre-clinical analysis of diagnostic or therapeutic agents. Likewise, the donor and recipient mammalian subject may be syngenic or xenogenic.

The donor and recipient subjects may both be healthy or diseased. In embodiments where either the donor or recipient mammalian subject mammalian subject is diseased, the donor and recipient subjects are paired such that the donor subject is capable of developing a granuloma comprising activating immune response cells or a particular subset of immune response cells (e.g., monocytes, macrophage, DCs, or T-cells) that are capable of homing to the inflammatory tissue in the recipient subject. Thus, in some embodiments, the donor subject may be healthy or diseased (e.g., immunocompromised for a specific subset of immune response cells or autoimmune for a specific antigen). The recipient subject may also be immunocompromised (e.g., nude mice). In some preferred embodiments, the recipient subject demonstrates non-systemic, localized inflammation (e.g., granuloma, cancer associated inflammation, cardiovascular inflammation, or autoimmune associated inflammation.).

Creating a Granuloma. A granuloma may be induced in the donor or recipient by administration of an inflammation-inducing agent such as caragennen or another mitogen (PhytohAEmagglutinin, Concanavalin A, or Staphylococcal protein A.) into the subject. In some embodiments, the inflammation-inducing agent is administered to the subject subcutaneously so that a focus of inflammation, in the form of a granuloma, develops at the site of injection. In alternative embodiments, the inflammation-inducing agent may be introduced into the subject by placement into a surgically created flap, which may be closed by any surgical means (e.g., suturing or ablation). The amount of inflammation-inducing agent may be empirically determined according to the weight and condition of the subject. In some particular embodiments, the amount of inflammation-inducing agent is approximately 150 μL of a 0.1% carrageen solution applied. When the agent is dispersed in a solution, the concentration should be adjusted such that the final volume introduced subcutaneously is sufficient to induce a granuloma, but minimized so that the surface area of the granuloma does not exceed about 0.5 cm to about 1 mm.

Isolating Cells. The granuloma-derived cells may be removed from the donor subject and enriched. The nucleated cells are separated from non-nucleated cells using any art-recognized technique such as gradient centrifugation. The nucleated granuloma-derived cells may be further enriched for a particular subset of immune reactive cell or cells using affinity techniques (e.g., immunobeads), and/or separation reagents (e.g., Ficoll). The granuloma-derived cells may be further activated or enriched for a specific population of immune response cell by applying of one or more cytokine or other immuno-stimulatory agents to the granuloma-derived cells.

Staining Cells with an Optical Agent. The granuloma-derived cells may be stained with any optical dye. The optical agent preferably comprises a dye that is biologically inert and non-toxic. In some embodiments, the optical dye binds to the cell surface. In some other embodiments, the optical dye permeates the cell membrane and is retain within the cell. In yet other embodiments, the optical dye binds to the cell surface and permeate the cell.

In all embodiments, the optical agent associates with the cell with an affinity such that a sufficient amount of the optical dye remains associated with the cell following introduction into the animal and migration to the focus of inflammation. In some embodiments, the optical agent comprises a cyanine dye, which may be a cell-permanent dye that enters into and is retained in a cell, for example Cye 7.5. A non-limiting list of fluorescent dyes that may be employed in the methods disclosed herein includes: Cy5, Cy5.5, Cy7, Cy7.5, CypHer, IRDye 800, IRDye 680, Atto 647, Atto 655, Atto 740, Dy652, Dy734, Alexa 647, Alexa 680, and Alexa 750.

Localized Inflammation in the Recipient Animal. The recipient subject may be selected from animals demonstrating localized inflammation. Alternatively, localized inflammation may be induced in the recipient subject using one or more methods, for example introduction of an inflammatory inducing agent or primed immune cells into the animal. Although the recipient subject need not necessarily have localized inflammation, the presence of such localized inflammation at a location remote from the location where the activated granuloma-derived cells from the donor subject stimulates granuloma-derived cell migrate from the site of introduction to the site of the localized inflammation. This migration, which is induced by cytokines and other homing factors, concludes when the activated granuloma-derived cells exit the vasculature, enter into, and reside at the interstitial spaces of the inflamed tissue.

Introducing Ex Vivo Cells into Recipient Animal. Introducing the granuloma-derived nucleated cells into a recipient mammalian subject at a site remote from site where the inflammatory agent was introduced. Any parental mode of introduction may be used, including intravenous, subcutaneous, intramuscular, or intraperitoneal introduction.

Imaging the recipient mammalian subject using an optical system. After the primed cells have been introduced into the recipient animal, they may be tracked and/or measured. Measurements may be qualitative or quantitative. Quantitative measures may include measurements of fluorescent intensity, localization and reconstruction of molecular targets, fluorescence concentration estimation, or and fluorescence lifetime.

Biodistribution Analysis. Distribution of the granuloma-derived cells in the recipient animal may be observed using an optical imaging device (e.g., eXplore Optix). Further analysis may include extracting specific tissue or organs (e.g., lung, spleen, or liver) from the animal and determining the absence or presence of optical signal associated with the granuloma-derived cells using, for example, an optical scanner. Organs (e.g., lung, spleen, and liver) and the granuloma was extracted and scanned under the optical scanner fitted with 785 nm laser diode. The lifetime analysis of the signals from these organs indicated the presence of dye labeled cells that has accumulated during the tail vein injection and the migration of dye tagged immune cells to the granulomas

EXAMPLES

Practice of the invention will be still more fully understood from the following examples, which are presented herein for illustration only and should not be construed as limiting the invention in any way.

All animal images were performed using the GE eXplore Optix device. The illumination occurs via a single fixed wavelength in the range of 440 nm to 780 nm according to the excitation wavelength of the particular optical agent used.

The system used was fitted with pulsed laser diode emitting at 4 different wavelengths 440 nm, 635 nm, 670 nm, and 785 nm. The choice of wavelengths applied ranged from near-infrared wavelength region to the visible region. During imaging, the bed moved into a dark chamber (imaging chamber) that contained the laser sources, filters, and detectors. The image analysis was processed with Optiview software and the signal collected was measured as Total Photon Count (TPC).

Immunocompromised nu/nu, 10-12 weeks old were purchased from Charles River. The nude mice strains were housed on a ventilated mouse rack mounted with an autoclaved cage assembly. Animals were fed with food and water ad libitum.

Example 1

Figure 1:
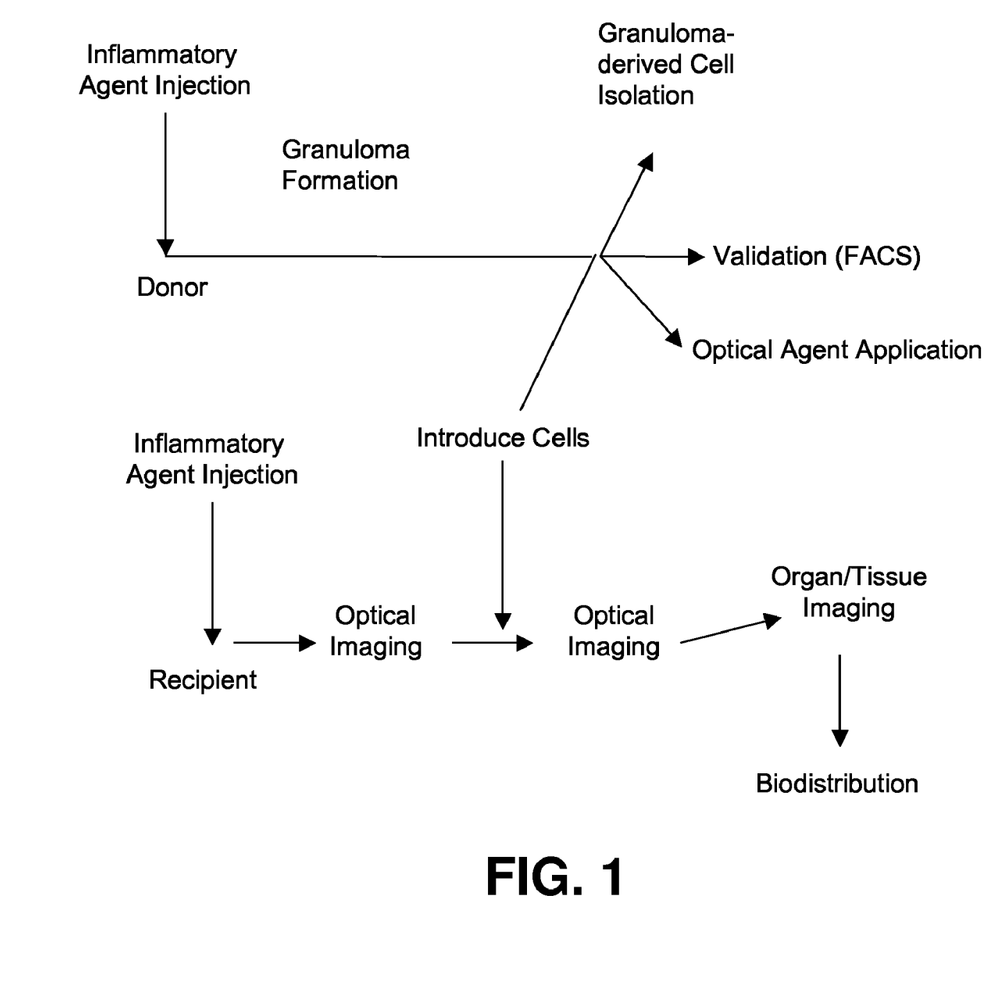
FIG. 1 shows a schematic representation of one embodiment of the present methods, in which granuloma-derived nucleated cells are removed from a donor animal, stained with an optically active agent, introduced into a recipient animal, and optically imaged.
Figure 2:
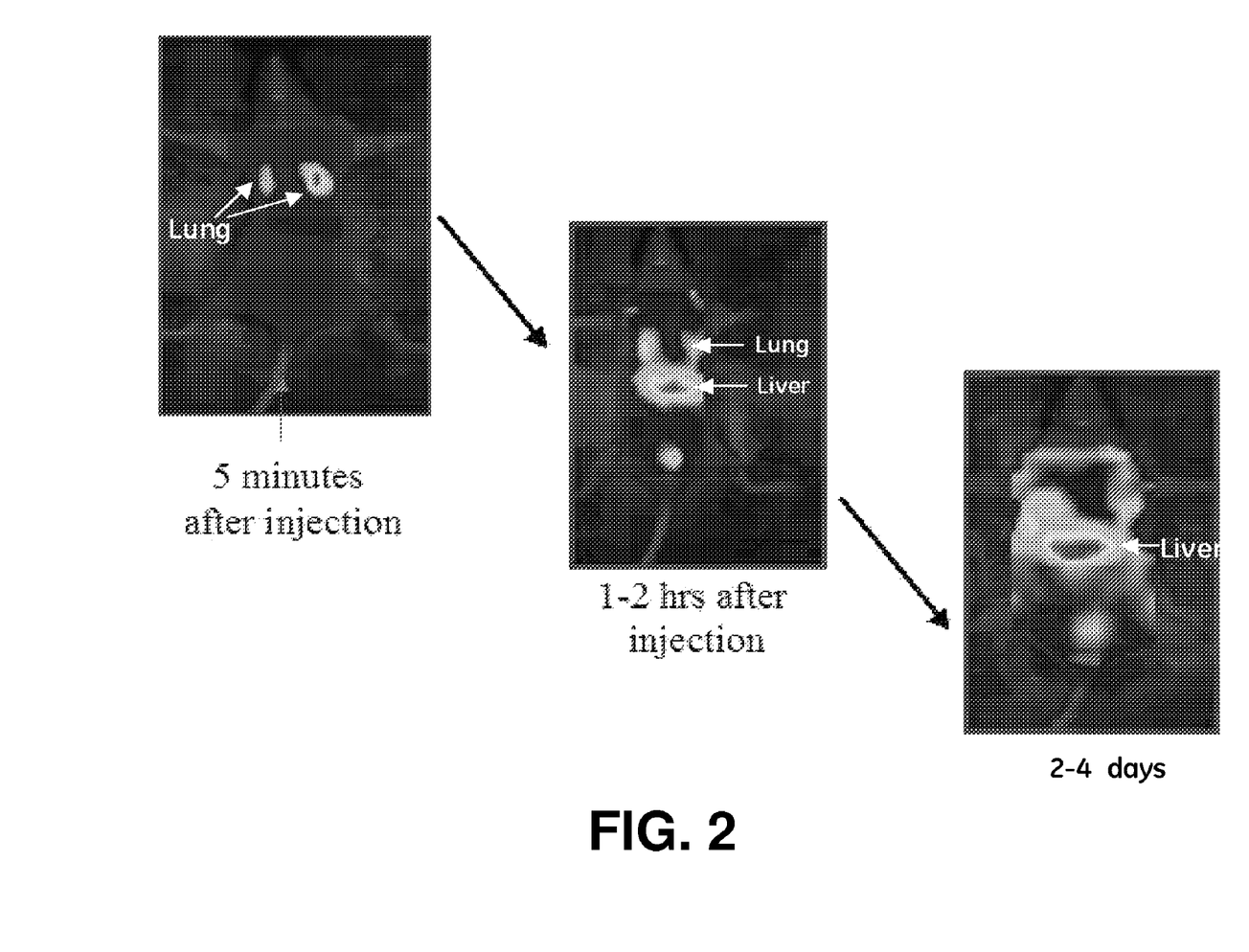
FIG. 2 shows the biodistribution of granuloma-derived nucleated cells tagged with an optical agent at various times following introduction of the cells into the recipient animal.
Figure 3:
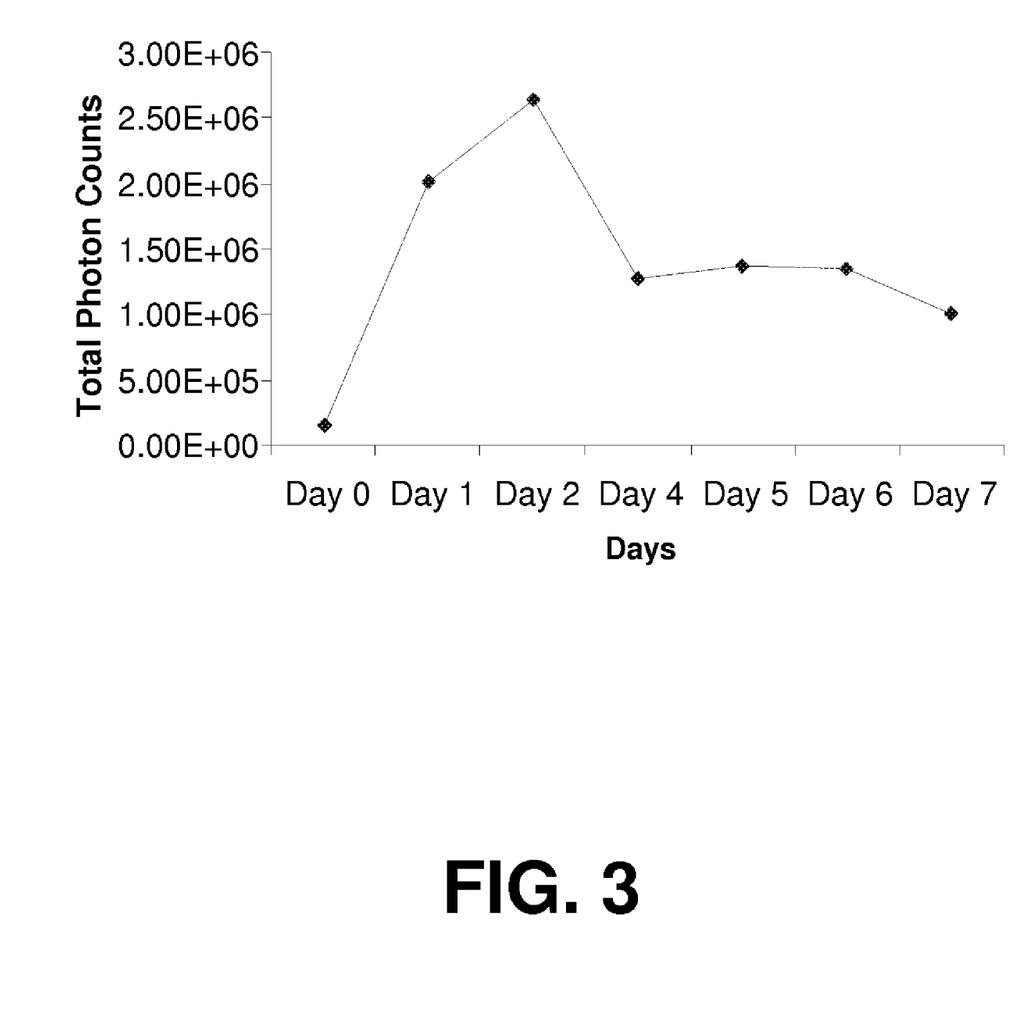
FIG. 3 shows the total photon counts for optically labeled, granuloma-derived nucleated cells following injection over the course of days. For the particular example depicted in FIG. 3, the granuloma-derived nucleated cells were stained using Cye 7.5-NHS ester.

A schematic representation of one experimental model is shown in FIG. 1. Set 1 (Donor Animals; Nu/nu mice (n=10)) were injected with 50 µl of 0.1% carageenan, subcutaneously for generating granuloma. The ganulomas were allowed to grow for about 4 days. The animals were sacrificed and the granuloma excised from the skin. The ganulomas were checked under microscope and cells extracted as described in the section below. The cells from the ganulomas of animals from Set 1 were then stained with Cy7.5-NHS ester.

Set 2 (Recipient Animals; Nu/nu mice (n=5)), were primed by injection of 150 µl of 0.1% carageenan, subcutaneously three days after Set 1. Thus, the Set 2 animals were in the process of granuloma growth for 24 hours when they receive 0.5 million of the granuloma-derived nucleated cells stained with Cy7.5-NHS ester. The granuloma-derived nucleated cells were injected into Set 2 Animals via tail vein. The cells migration was tracked noninvasively from animals using eXplore Optix scanner in the Set 2 Animals.

Example 2

Collecting cells from Granuloma. A time study of the granuloma was conducted on animal ages versus granuloma maturity rate. Animals 10-12 weeks old were chosen for generating granulomas. After 4 days of carageenan injection, the animals were sacrificed and granuloma removed from the underside of the skin and washed in sterile PBS. The cells from the granulomas were scraped using sterile razors, checked viability, and counted under the microscope. The granuloma mass was minced thoroughly and passed through sieve (MACS Pre-Separation Filter, Miltenyi Biotech Cat. No. 130-041-407) to separate free cells from the granuloma. The flow-through was centrifuged, and cells from 10 animals pooled and counted. The cells were checked for viability using Trypan blue. 100 µl of cell suspension was set aside to test for cellular population by FACS analysis. Visual inspection and FACS confirmed approximately 100% viability.

Example 3

Density Gradient Centrifugation. Pooled cells were washed once with PBS and resuspended in 5 ml of PBS. The cell suspension was layered on 5 ml of Lympholyte M (Lympholyte M, Cedarlane Labs Cat. No CL5031) and centrifuged for 20 minutes at 1500 g. The cell layer was isolated, washed with PBS three times (500 g for 5 minutes), and counted. 100 µl of cell suspension set aside to test for cellular population and viability test by FACS analysis. The rest of the cells were stained with Cy7.5 NHS-ester dye as described below. The RBCs pelleted down from the mixture and the band of nucleated cells from the middle of the tube was collected.

Example 4

Cell Staining. 1 µg of Cy 7.5-NHS ester was mixed in 10 ml of PBS. The cells are resuspended in the buffer and left on ice for 20 minutes. Cells were washed three times in PBS and the cell pellet is placed under Optix scanner to confirm cell staining. The cells were resuspended in PBS and 100 µl of the cell suspension (containing $0.5 \times 10^6$ cells/100 µl) was injected via the tail vein. The stained cell pellet generated signal that was detected by the scanner.

Example 5

FACS Analysis to Determine Cell Viability. Stained cells were washed three times in PBS and resuspended in 100 µl PBS. The cell suspension was incubated with 20 µl of 7-AAD for 20 minutes at room temperature. The cells are washed once in PBS and resuspended in 500 µl of PBS, then analyzed in FACS for viability.

Example 6

FACS Analysis for Cellular Markers. The cells were stained with cell markers for leukocytes (CD45) and monocyte/macrophage (CD 11 b). Both CD11b and CD45 antibodies were purchased from Miltenyi Biotec and stained following vendors instructions. Thus, 10 µl of CD11b PE antibody and 10 µl CD45 FITC were incubated with $1 \times 10^6$ cells for 20 minutes. The cells were washed in PBS, resuspend in 0.5 mL PBS, and run on Flow Cytometer (Beckman Coulter FC500 MPL). The cells were viable after staining with Cye7.5 NHS-ester and 72% of cell population in the suspension were positive for CD45 and CD11b.

Example 7

Cell Injection. Nude mice from Set 2 bearing 2-day-old granuloma, were injected with cells stained with Cy7.5 NHS-ester. In preparation for the injection, the tail was warmed using heat lamp for 5 minute and 100 µl of the cell suspension (containing $0.5 \times 10^6$ cells/100 µl) was injected via the tail vein. Following injection, animals were anesthetized and imaged under the eXplore Optix scanner in supine position to track the cell movement.

Example 8

General Animal Imaging Protocols. The eXplore Optix laser driver was allowed to warm up for 20 minutes prior to imaging. Animals from Set 2 were placed under the Optix scanner in both supine and prone position and whole-body preinjection scan was recorded. Animals were anesthetized using 2% isoflurane and placed in a supine position on the scanner stage warmed at 37° C. The animals were kept under 1% isoflurane during the scan. Each animal was imaged under 785 nm laser separately, with a LP (Laser Power) of 500 PW, IT (integration time) of 1.0s, and SS (scan step) of 3 mm for whole body scan. When selecting the granuloma area only, the scan step in reduced to 1.5 mm.

Animals from Set 2 were scanned under supine and prone position, 5 minutes after injecting cells via tail vein. The mouse receiving a good injection shows signal from both lungs when placed supine position under the scanner within 5 minutes of receiving injection. The animals were rescanned every 24 hours for 10 days to monitor cell trafficking to the granuloma site.

The Cye dye stained granuloma-derived nucleated cells were observed to travel to lung and reside predominantly in the liver area after 24 hours of injection. The signal from the lung and liver decreases with time and it can be further studied by using lifetime image analysis. When an animal was imaged in prone position, we also detected signal (Total Photon Count) from the granuloma within 24 hours after injection, indicating the trafficking of monocytes to the site of inflammation.

Figure 4A:
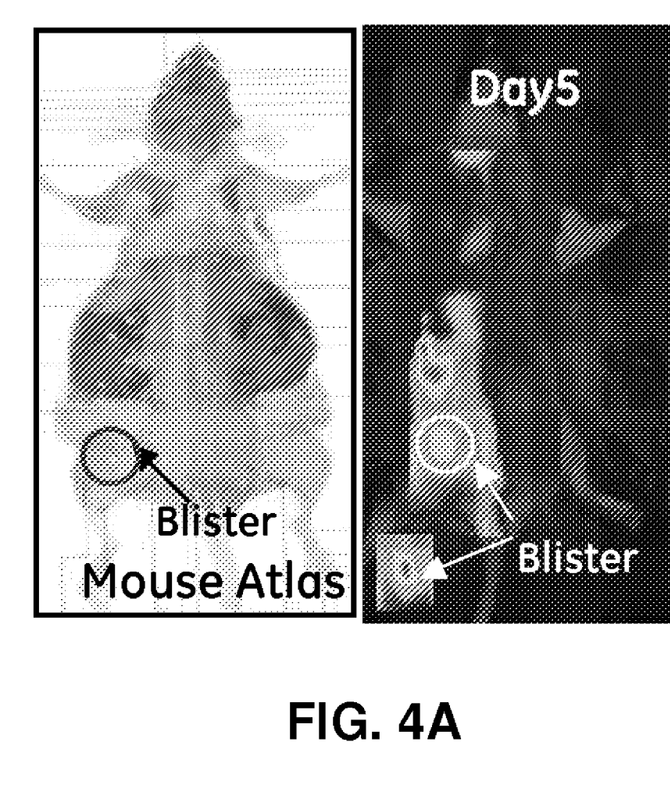
Figure 4B:
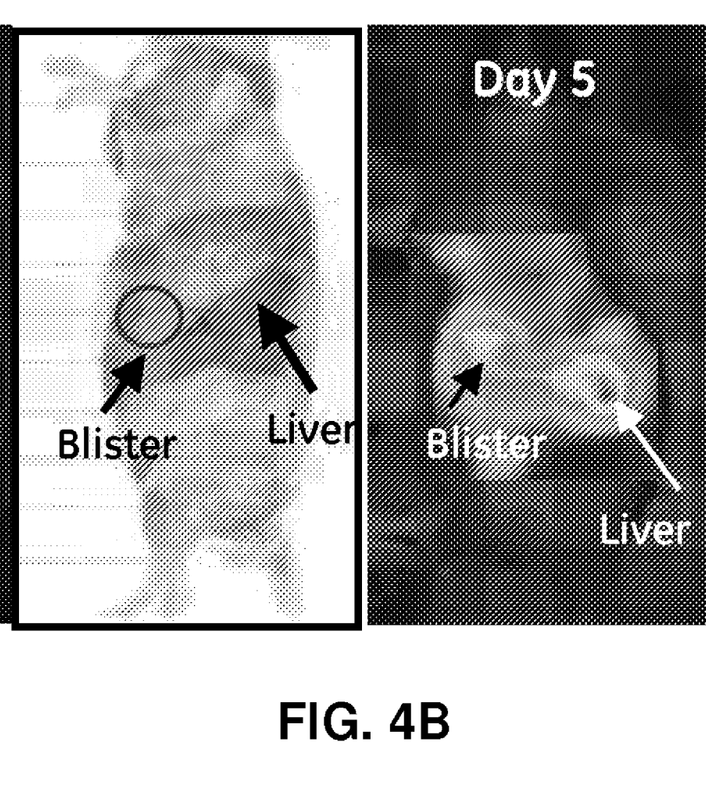
Figure 5A:
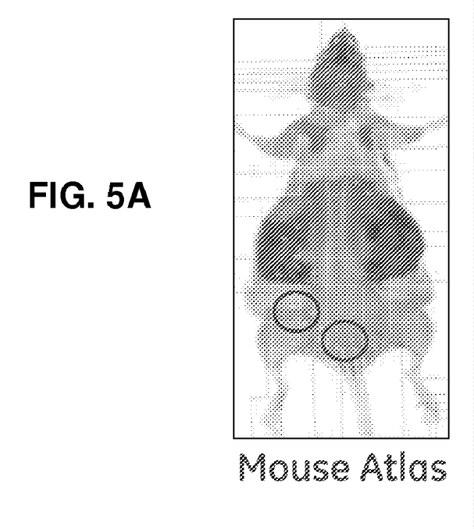
FIG. 5 shows the granuloma localization of granuloma-derived nucleated cells in a recipient animal in a prone position at day 5 (FIG. 5B; CD1 mouse) and at day 9 (FIG. C; nude mouse).
Figure 5B:
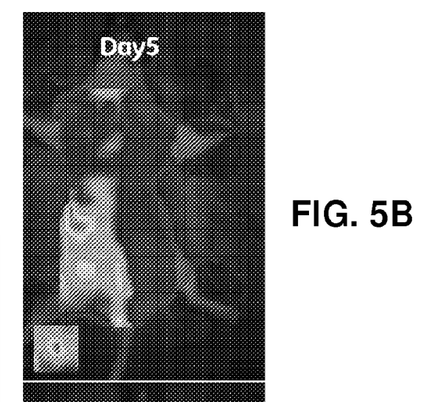
Figure 5C:
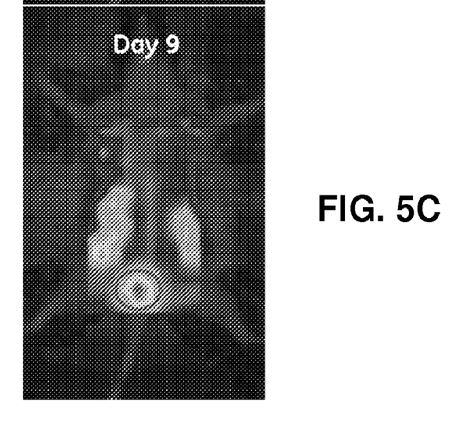

The signal increases until 48 hours and then decreased with time. However the signal enhances in the images after day 5, as the cell signal from the liver and spleen diminishes (FIG. 4). The imaging model was repeated several times with consistent results.

Example 9

Lifetime Imaging. The OptiView software was used for Lifetime analysis. The software could resolve the intensity signal arising from different sources of fluorescence having different lifetime. Lifetime analysis was done using a time domain-curve referred to as TPSF (temporal point spread function). The data analysis was generated from clean data of the fluorescence images. The clean data was used for acquiring (1) intensity, (2) TPSF curve, and (3) lifetime histogram.

TPSF curve is drawn from the signal derived from the granuloma site. The TPSF curve from the granuloma site is similar to the cell pellet stained with the dye before injection.

Figure 6:
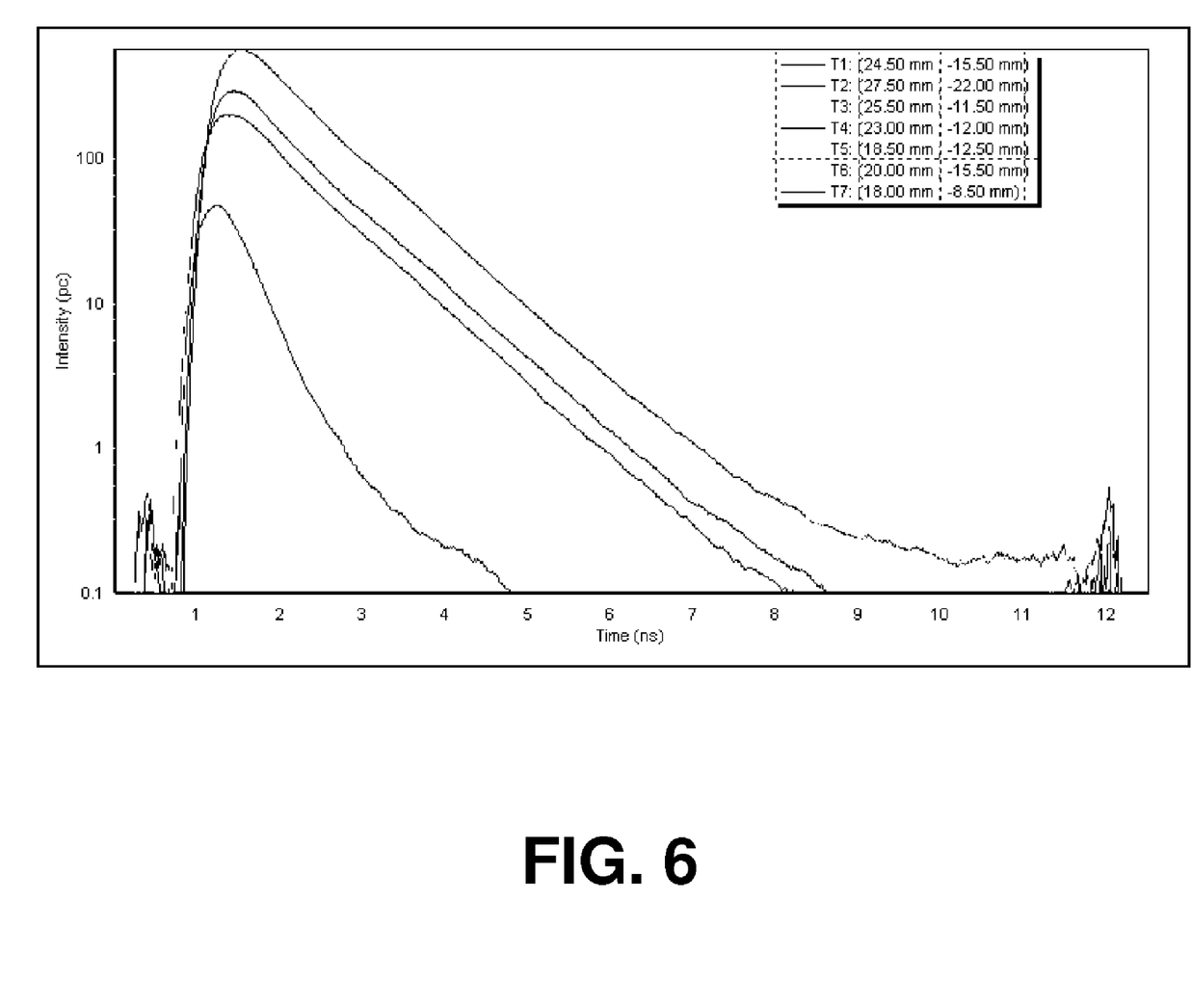
FIG. 6 shows the TPSF curve derived from granuloma of animals imaged at approximately 24 hour intervals as follows: T1 (granuloma before cell injection); T2 (post-injection Day 1); T3 (post-injection Day 2); T4 (post-injection Day 4); T5 (post-injection Day 5); T6 (post-injection Day 6); and T7 (post-injection Day 7).

As shown in FIG. 6, the TPSF curve derived from granuloma of animals imaged at approximately 24 hour intervals as follows: T1 (granuloma before cell injection); T2 (post-injection Day 1); T3 (post-injection Day 2); T4 (post-injection Day 4); T5 (post-injection Day 5); T6 (post-injection Day 6); and T7 (post-injection Day 7). As the graph in FIG. 6 shows, the TPSF curve from the granuloma site at preinjection (background signal) is distinct from the TPSF curve post-injection (indicating that fluorescent labeled cells are present in the granuloma). FIG. 6 also shows that the TPSF curves follow a common pattern for each of the post-injection time points during a 7-day interval.

EQUIVALENTS

The invention may be embodied in other specific forms without departing from the spirit or essential characteristics thereof. The foregoing embodiments are therefore to be considered in all respects as illustrative rather than limiting on the invention described herein. The scope of the invention is thus indicated by the appended claims rather than by the foregoing description, and all changes that come within the meaning and range of equivalency of the claims are therefore intended to be embraced therein.

The invention claimed is:
1. A method of monitoring inflammatory cell migration in a mammal comprising the steps of:
   (a) providing a donor mammalian subject;
   (b) introducing an inflammatory agent into the donor mammal to create a granuloma;

(c) isolating granuloma-derived nucleated cells from the granuloma of the donor mammalian subject;
(d) labeling the granuloma-derived nucleated cells of step (c) with a fluorescent dye, wherein the fluorescent dye is selected from the group consisting of Cy5, Cy5.5, Cy7, Cy7.5, CypHer, IRDye 800, IRDye 680, Atto 647, Atto 655, Atto 740, Dy652, Dy734, Alexa 647, Alexa 680, or Alexa 750;
(e) providing a recipient mammalian subject with inflamed tissue;
(f) introducing the granuloma-derived nucleated cells of step (d) into the recipient mammalian subject at a site remote from the inflamed tissue; and
(g) imaging the recipient mammalian subject using an optical system capable of detecting the fluorescent dye.

2. The method of claim 1, wherein the mammalian subjects are selected from mouse, rat, and guinea pig.

3. The method of claim 1, wherein the donor mammalian subject, the recipient mammalian subject, or both the donor mammalian subject and the recipient mammalian subject is immunocompromised.

4. The method of claim 1, wherein donor mammalian subject and the recipient mammalian subject are histocompatible with each other.

5. The method of claim 1, wherein the inflammatory agent is Carrageenan, PhytohAEmagglutinin, Concanavalin A, or Staphylococcal protein A.

6. The method of claim 1, wherein the granuloma-derived cells are monocytes, macrophage, dendritic cells (DCs), polynuclear monocytes (PNMs), eosinophils, neutrophils, T cells, or combinations thereof.

7. The method of claim 1, wherein the inflammatory agent is introduced into the donor mammalian subject subcutaneously.

8. The method of claim 1, wherein the isolating step (c) occurs about 1 day, about 3 days, or about 6 days after the introducing step (b).

9. The method of claim 1, wherein the granuloma-derived nucleated cells isolated in step (c) are enriched using anti-CD45, anti-CD11b, or a combination of anti-CD45 and anti-CD11b.

10. The method of claim 1, wherein the fluorescent dye is a cyanine dye or a rotaxane dye.

11. The method of claim 1, wherein the granuloma-derived nucleated cells are introduced into the recipient mammalian subject intravenously.

12. The method of claim 1, wherein about 0.25 million to about 5 million granuloma-derived nucleated cells are introduced into the recipient mammalian subject.

13. The method of claim 1, wherein the optical imaging step (f) is performed at a wavelength frequency of about 440 nm to about 800 nm.

14. The method of claim 13, wherein the wavelength frequency is about 766 nm to about 800 nm.

15. The method of claim 1, further comprising the step of determining the presence of the ex vivo cells in the recipient mammalian subject using total photon counts.

16. The method of claim 15, wherein the total photon counts are measured at from about 5 minutes to about 10 days after the introduction of the granuloma-derived nucleated cells into the recipient mammalian subject.

17. A method of monitoring inflammatory cell migration in a mammal comprising the steps of:
(a) providing a donor mammalian subject;
(b) introducing an inflammatory agent into the donor mammal to create a granuloma;
(c) isolating granuloma-derived nucleated cells from the granuloma of the donor mammalian subject;
(d) labeling the granuloma-derived nucleated cells of step (c) with a fluorescent dye, wherein the fluorescent dye is selected from the group consiting of Cy5, Cy5.5, Cy7, Cy7.5, CypHer, IRDye 800, IRDye 680, Atto 647, Atto 655, Atto 740, Dy652, Dy734, Alexa 647, Alexa 680, or Alexa 750;
(e) introducing the inflammatory agent into a recipient mammalian subject;
(f) introducing the granuloma-derived nucleated cells of step (d) into the recipient mammalian subject at a site remote from site where the inflammatory agent was introduced in step (e); and
(g) performing a biodistribution study to determine the presence of the granuloma-derived nucleated cells in the recipient mammalian subject, wherein the biodistribution study comprises optically imaging the recipient mammalian subject using an optical system capable of detecting the fluorescent dye.

18. The method of claim 17, wherein the mammalian subjects are selected from mouse, rat, and guinea pig.

19. The method of claim 17, wherein the donor mammalian subject, the recipient mammalian subject, or both the donor mammalian subject and the recipient mammalian subject is immunocompromised.

20. The method of claim 17, wherein donor mammalian subject and the recipient mammalian subject are histocompatible with each other.

21. The method of claim 17, wherein the inflammatory agent is carrageenan, pytohemagglutinin, concanavalin A, or staphylococcal protein A.

22. The method of claim 17, wherein the granuloma-derived cells are monocytes, macrophage, dendritic cells (DCs), polynuclear monocytes (PNMs), eosinophils, neutrophils, T cells, or combinations thereof.

23. The method of claim 17, wherein the inflammatory agent is introduced into the donor mammalian subject subcutaneously.

24. The method of claim 17, wherein the isolating step (c) occurs about 1 day, about 3 days, or about 6 days after the introducing step (b).

25. The method of claim 17, wherein the granuloma-derived nucleated cells isolated in step (c) are enriched using anti-CD45, anti-CD11b, or a combination of anti-CD45 and anti-CD 11b.

26. The method of claim 17, wherein the fluorescent dye is a cyanine dye or a rotaxane dye.

27. The method of claim 17, wherein the granuloma-derived nucleated cells are introduced into the recipient mammalian subject intravenously.

28. The method of claim 17, wherein about 0.25 million to about 5 million granuloma-derived nucleated cells are introduced into the recipient mammalian subject.

29. The method of claim 17, wherein the optical imaging is performed at a wavelength frequency of about 440 nm to about 800 nm.

30. The method of claim 29, wherein the wavelength frequency is about 766 nm to about 800 nm.

31. The method of claim 17, further comprising the step of determining the presence of the ex vivo cells in the recipient mammalian subject using total photon counts.

32. The method of claim 31, wherein the total photon counts are measured at from about 5 minutes to about 10 days after the introduction of the granuloma-derived nucleated cells into the recipient mammalian subject.

33. The method of claim 17, wherein the biodistribution analysis comprises extracting liver, spleen, lungs, or tumor tissue from the recipient mammalian subject and optically imaging the extracted tissue.

34. The method of claim 17, wherein the optical imaging is accomplished using an optical scanner, a microscope, or a fluorescent activated cell sorter.

35. The method of claim 33, wherein an intensity of fluorescent emission of the fluorescent dye present in the extracted tissue is measured and correlated to the amount of granuloma-derived nucleated cells in the extracted tissue.

* * * * *